(12) United States Patent
Okano

(10) Patent No.: US 8,514,482 B2
(45) Date of Patent: Aug. 20, 2013

(54) TERAHERTZ ELECTROMAGNETIC WAVE GENERATING ELEMENT

(75) Inventor: Masato Okano, Osaka (JP)

(73) Assignee: Nalux Co., Ltd., Osaka (JP)

( * ) Notice: Subject to any disclaimer, the term of this patent is extended or adjusted under 35 U.S.C. 154(b) by 110 days.

(21) Appl. No.: 13/272,638

(22) Filed: Oct. 13, 2011

(65) Prior Publication Data

US 2012/0050841 A1  Mar. 1, 2012

Related U.S. Application Data

(63) Continuation of application No. PCT/JP2010/002558, filed on Apr. 7, 2010.

(30) Foreign Application Priority Data

Apr. 16, 2009 (WO) .................. PCT/JP2009/001769

(51) Int. Cl.
 *G02F 1/35* (2006.01)
 *G02F 2/02* (2006.01)
 *H01S 3/10* (2006.01)

(52) U.S. Cl.
 USPC .......... 359/326; 359/328; 359/330; 359/332; 372/21; 356/328

(58) Field of Classification Search
 USPC ................... 359/326, 328, 330, 332; 372/21
 See application file for complete search history.

(56) References Cited

U.S. PATENT DOCUMENTS

| 7,710,637 B2 | 5/2010 | Ikari et al. | |
|---|---|---|---|
| 2006/0139755 A1* | 6/2006 | Kersting et al. | 359/566 |
| 2009/0021825 A1* | 1/2009 | Dunn et al. | 359/330 |
| 2013/0075629 A1* | 3/2013 | Doi et al. | 250/504 R |

FOREIGN PATENT DOCUMENTS

| EP | 1821141 | 8/2007 |
|---|---|---|
| JP | 2005-099453 | 4/2005 |
| JP | 2005-284232 | 10/2005 |
| JP | 2006-163026 | 6/2006 |
| JP | 2009-058875 | 3/2009 |
| JP | 2009-80448 A | 4/2009 |

(Continued)

OTHER PUBLICATIONS

Wagner-Genter, A. et al., "Low Loss THz Window", Infrared Physics & Technology; vol. 48, Feb. 21, 2006, pp. 249-253.

(Continued)

*Primary Examiner* — Hemang Sanghavi
(74) *Attorney, Agent, or Firm* — Squire Sanders (US) LLP

(57) ABSTRACT

A terahertz electromagnetic wave generating element can include a generation layer, and a plurality of pairs of layer structures provided on opposite sides thereof. The layer structures are each provided with a first layer, a second layer on the side of the first layer opposite to the generation layer, and a first grating and a second grating, and having a grating period smaller than the wavelength of the terahertz electromagnetic wave to be used. The first and second gratings are configured so that the refractive index of a medium between the first layer and the second layer continuously varies between a first refractive index and a second refractive index. The thickness of the first and second layers and the grating period, and the grating height are determined so that a terahertz electromagnetic wave having a desired bandwidth with respect to a central wavelength of the terahertz electromagnetic wave generated by the generation layer can be generated.

11 Claims, 13 Drawing Sheets

(56) References Cited

FOREIGN PATENT DOCUMENTS

| JP | 2009-204900 | 9/2009 |
|---|---|---|
| JP | 2009-217085 | 9/2009 |
| WO | 2006062073 | 6/2006 |

OTHER PUBLICATIONS

Bruckner, C., et al., "Broadband Antireflective Surface-Relief Structure for THz Optics," Optics Express, vol. 15, No. 3, Feb. 5, 2007, pp. 779-789.
Shin-ichi Kuroo, et al, "Reduction of Reflection from Silicon Surface by Means of Sub-Wavelength Patterning in Terahertz Region,", 29p-ZH-3, The Japan Society of Applied Physics and Related Societies, No. 3, Mar. 27, 2008, pp. 1168.
H. Shirai et al., "Enhancement of Terahertz Wave Generation by Terahertz One-Dimensional Photonic Crystal," 28p-ZH-7,The Japan Society of Applied Physics and Related Societies, No. 3, Mar. 27, 2008, pp. 1160.
Hiroki Fukuda, "Fabrication of an Antireflection Structured Surface," No. 20, Oct. 31, 2006, pp. 81-86.
Adrian Dobroiu et al., "THz-Wave Spectroscopy Applied to the Detection of Illicit Drugs in Mail," Proceedings of the IEEE, vol. 95, No. 8, Aug. 2007, pp. 1566-1575.
Hiroshi Toyota, et al., "Fabrication of Microcone Array for Antireflection Structured Surface Using Metal Dotted Pattern," Japanese Journal of Applied Physics, vol. 40, Part 2, No. 7B, Jul. 15, 2001, pp. L747-L749.
Pengyu Han, et al, "Application of Silicon Micropyramid Structures for Antireflection of Terahertz Waves," IEEE Journal of Selected Topics in Quantum Electronics, vol. 16, No. 1, Feb. 5, 2010, pp. 338-343.
International Search Report and Written Opinion corresponding to International Application No. PCT/JP2010/002558 dated May 25, 2010.
Noriaki Tsurumachi et al., "Enhancement of Optical Rectification for THz Amplification in One-Dimensional Photonic Crystals", 33rd International Conference on Infrared, Millimeter, and Terahertz Waves, Sep. 15, 2008, 2 pages.
Claudia Bruckner et al., "Broadband Antireflective Surface-Relief Structure for THz Optics", Optics Express 779, vol. 15, No. 3, Feb. 5, 2007, 11 pages.
Toshiaki Hattori et al., "Analysis of Optical Nonlinearity by Defect States in One-Dimensional Photonic Crystals", J. Opt. Soc. Am. B/vol. 14, No. 2, Feb. 1997, 8 pages.
S. Kuroo et al., "Triangular Surface-Relief Grating for Reduction of Reflection from Silicon Surface in the 0.1-3 Terahertz Region", IEEE 2008, 2 pages.
European Search Report application No. 10764233.2 dated Aug. 28, 2012.
European Office Action application No. 10 764 233.2 dated Sep. 14, 2012.

\* cited by examiner $$F(h) = \frac{f(h)}{\Lambda}$$

FIG. 5A
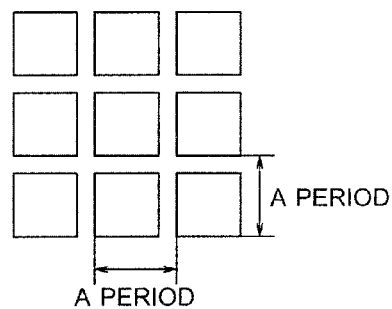
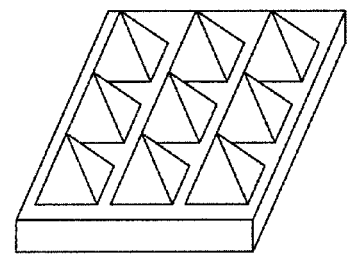
FIG. 5B
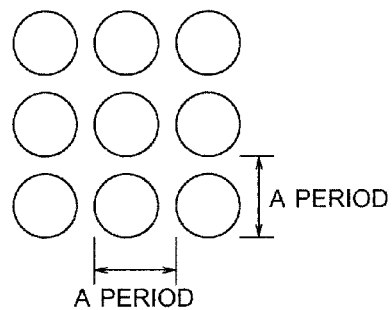
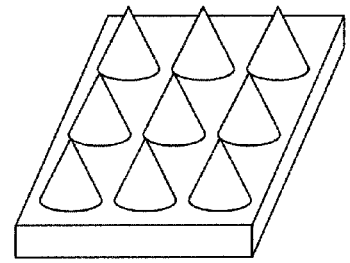

FIG. 5C
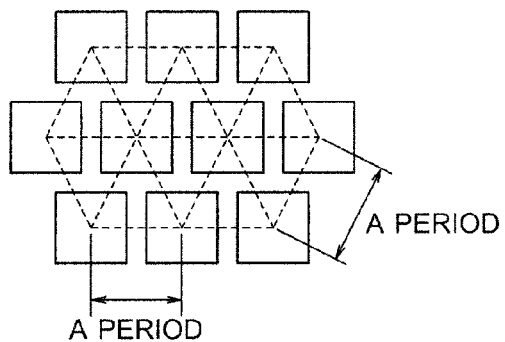
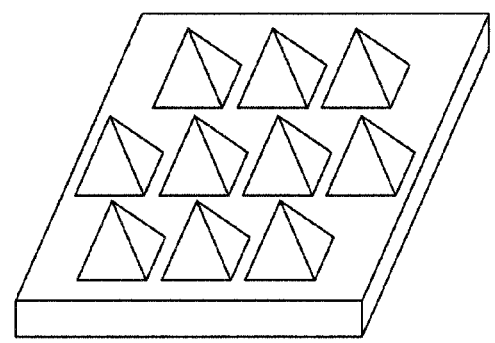
FIG. 5D
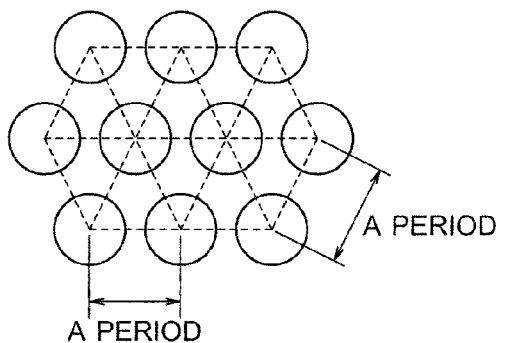
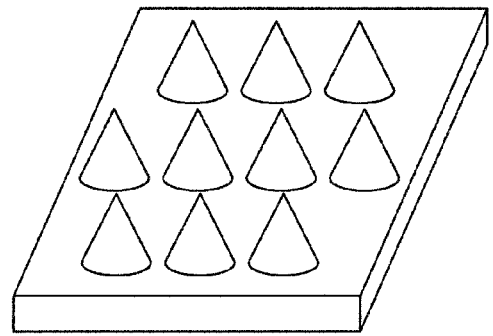

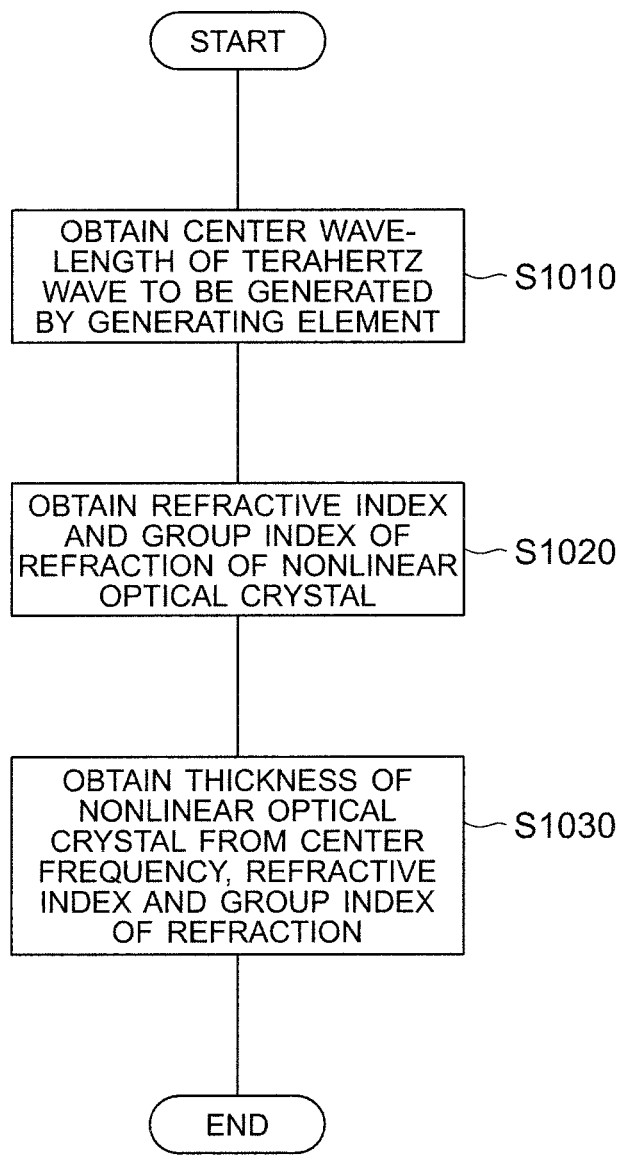

TERAHERTZ ELECTROMAGNETIC WAVE GENERATING ELEMENT

FIELD OF THE INVENTION

The present invention relates to a terahertz electromagnetic wave generating element which generates terahertz electromagnetic wave with a high efficiency.

BACKGROUND ART

Frequency of terahertz electromagnetic wave ranges from 0.1 THz to 10 THz and its wavelength ranges from 30 micrometers to 3 millimeters. That is, the frequency range of terahertz electromagnetic wave is a boundary range between light wave and radio wave. Accordingly, terahertz electromagnetic wave passes through a substance like radio wave and travels in a straight line like light. Information on structures and behaviors of molecules can be obtained in the frequency range of terahertz electromagnetic wave, and therefore applications of terahertz electromagnetic wave in a various fields are anticipated. The fields include information and communication, nondestructive inspection, security field including detection of dangerous and hidden items, biomedical field including imaging of a malignant tumor, field of agriculture, field of industry, field of environment and field of space.

As a method for generating terahertz electromagnetic wave, a method in which nonlinear optical crystal is illuminated with femtosecond pulse laser to generate terahertz electromagnetic wave is known (JP2005-99453A, for example). When nonlinear optical crystal is illuminated with such a strong light as that of femtosecond pulse laser, polarization develops and vanishes in the nonlinear optical crystal and these phenomena are substantially identical with generation of pulsed current. As a consequence, the nonlinear optical crystal generates terahertz electromagnetic wave.

However, in the frequency range of terahertz electromagnetic wave, refractive index of a substance becomes higher because of dispersion. Accordingly, many components are reflected or absorbed by the substance when terahertz electromagnetic wave passes through the substance and therefore output of terahertz electromagnetic wave will be reduced. In order to prevent reduction in output of terahertz electromagnetic wave, an attempt that a thin film is provided on a surface of nonlinear optical crystal to reduce reflection on the surface has been made. However, efficiency of energy conversion into terahertz electromagnetic wave has not been remarkably enhanced because of the absence of a thin film material which is effective in the frequency range of terahertz electromagnetic wave and because of the existence of dispersibility of the thin film itself.

It is known that some materials easily transmit terahertz electromagnetic wave in a specific frequency band. An inspection system in which prohibited drugs, explosive items and the like are detected using the above-described feature, has been studied. Thus, in order to detect a specific substance, it is required to generate terahertz electromagnetic wave in the frequency band which is determined by the specific substance with energy conversion efficiency as high as possible.

Accordingly, there is a need for a terahertz electromagnetic wave generating element which generates terahertz electromagnetic wave in the predetermined frequency band with energy conversion efficiency as high as possible.

SUMMARY OF THE INVENTION

A terahertz electromagnetic wave generating element according to the present invention includes a generating layer made of nonlinear optical substance which emits terahertz electromagnetic wave from a surface when another surface is illuminated by light; and a multiple pairs of layer structures provided on the both sides of the generating layer. Each of the multiple pairs of layer structures includes a first layer; a second layer provided on a side of the first layer, the side being opposite to the side of the generating layer; a first grating provided on a surface on the generating layer side of the second layer, the first grating having a first period smaller than wavelength of used terahertz electromagnetic wave and a first height; and a second grating provided on a surface on the side opposite to the generating layer of the second layer, the second grating having the first period and the first height. Refractive index of a medium of the first layer (a first refractive index) is smaller than refractive index of a medium of the second layer (a second refractive index). The first grating and the second grating are constructed in such a way that refractive index between the first layer and the second layer gradually changes between the first refractive index and the second refractive index. Thickness of the first layer, thickness of the second layer, the first period and the first height are determined in such a way that terahertz electromagnetic wave having a desired band width is generated around the center wavelength of the generated terahertz electromagnetic wave.

By the use of the terahertz electromagnetic wave generating element according to the present invention, energy of terahertz electromagnetic wave can be concentrated into the desired band width. Accordingly, terahertz electromagnetic wave in the desired band width can be generated with a high efficiency.

In a terahertz electromagnetic wave generating element according to an embodiment of the present invention, the first period is determined in such a way that terahertz electromagnetic wave of frequencies on and above the upper limit of the desired band width is removed as much as possible.

According to the present embodiment, by the first and second gratings provided on the both sides of the second layer, terahertz electromagnetic wave of frequencies on and above the upper limit of the desired band width is diffracted and removed.

In a terahertz electromagnetic wave generating element according to another embodiment of the present invention, protruding portions of the first and second gratings are shaped like a cone.

According to the present embodiment, since the protruding portions of the first and second gratings are shaped like a cone, refractive index can be gradually changed between the first layer and the second layer.

In a terahertz electromagnetic wave generating element according to another embodiment of the present invention, protruding portions of the first and second gratings are shaped like a circular cone.

According to the present embodiment, since the protruding portions of the first and second gratings are shaped like a circular cone, refractive index can be gradually changed between the first layer and the second layer.

In a terahertz electromagnetic wave generating element according to another embodiment of the present invention, protruding portions of the first and second gratings are shaped like a pyramid.

According to the present embodiment, since the protruding portions of the first and second gratings are shaped like a pyramid, refractive index can be gradually changed between the first layer and the second layer.

In a terahertz electromagnetic wave generating element according to another embodiment of the present invention, protruding portions of the first and second gratings are made of the same material as a material of the second layer.

According to the present embodiment, since protruding portions of the first and second gratings are made of the same material as a material of the second layer, refractive index can be continuously changed between the first layer and the second layer.

In a terahertz electromagnetic wave generating element according to another embodiment of the present invention, the first and second gratings are one-dimensionally arranged.

According to the present embodiment, by the one-dimensionally arranged gratings, output of terahertz electromagnetic wave having a predetermined plane of polarization can be increased. More specifically, terahertz electromagnetic wave having a plane of polarization which is perpendicular to the longitudinal direction of the protrusion portions of the one-dimensionally arranged gratings can be prevented from decaying.

In a terahertz electromagnetic wave generating element according to another embodiment of the present invention, the first and second gratings are two-dimensionally arranged.

According to the present embodiment, by the two-dimensionally arranged gratings, output of terahertz electromagnetic wave can be increased independently of orientation of the plane of polarization.

In a terahertz electromagnetic wave generating element according to another embodiment of the present invention, a medium of the first layer is air.

According to the present embodiment, since air is used as the medium, the first layer can be formed easily.

In a terahertz electromagnetic wave generating element according to another embodiment of the present invention, a support shaped like a frame is provided to form the first layer.

According to the present embodiment, by the support shaped like a frame, the first layer the medium of which is air can be formed.

In a terahertz electromagnetic wave generating element according to another embodiment of the present invention, the second layer and the support shaped like a frame are integrally formed.

According to the present embodiment, since the second layer and the support shaped like a frame are integrally formed, the manufacturing process is simplified.

In a terahertz electromagnetic wave generating element according to another embodiment of the present invention, a medium of the second layer is polypropylene.

In a terahertz electromagnetic wave generating element according to another embodiment of the present invention, the nonlinear optical substance is crystal of zinc telluride (ZnTe).

An object inspection system according to another aspect of the present invention includes the terahertz electromagnetic wave generating element according to the present invention.

In the object inspection system according to the present aspect, detection can be carried out with a higher accuracy because output of the terahertz electromagnetic wave generating element is larger.

BRIEF DESCRIPTION OF THE DRAWINGS

FIG. 5A shows a two-dimensionally arranged grating in which pyramid protrusion portions are arranged like tetragonal lattice;

FIG. 5B shows a two-dimensionally arranged grating in which circular cone protrusion portions are arranged like tetragonal lattice;

FIG. 5C shows a two-dimensionally arranged grating in which pyramid protrusion portions are arranged like hexagonal lattice;

FIG. 5D shows a two-dimensionally arranged grating in which circular cone protrusion portions are arranged like hexagonal lattice;

FIG. 6 is a flowchart for illustrating how to design a nonlinear optical crystal which generates terahertz electromagnetic wave having a desired center wavelength;

MODE FOR CARRYING OUT THE INVENTION

Figure 1:
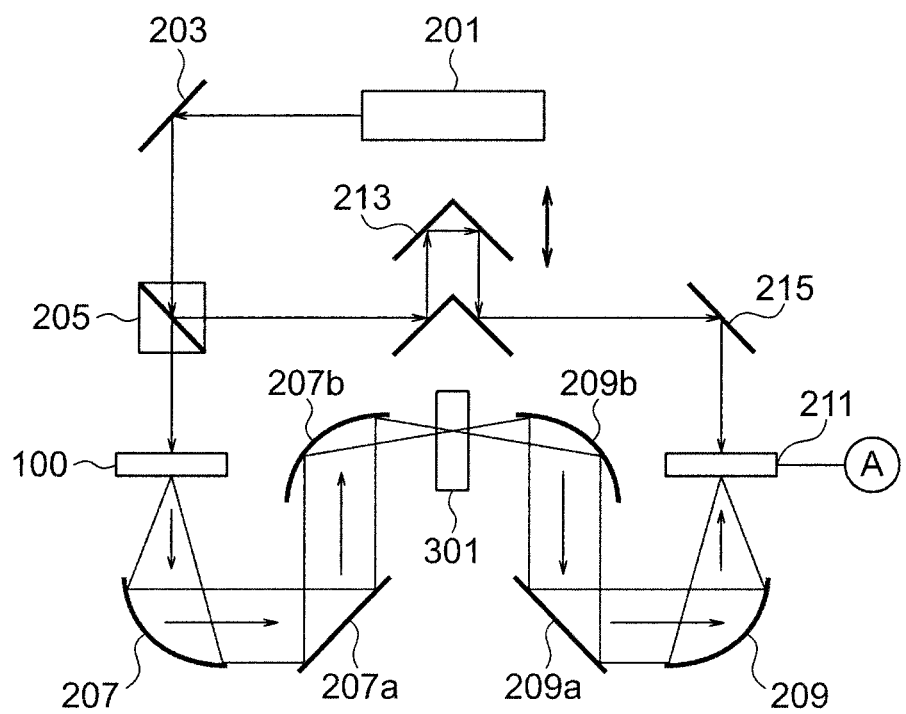
FIG. 1 shows a configuration of an object inspection system including a terahertz electromagnetic wave generating element.

FIG. 1 shows a configuration of an object inspection system including a terahertz electromagnetic wave generating element. In FIG. 1, laser beam emitted by a femtosecond laser 201 is reflected by a reflecting mirror 203 and reaches a beam splitter 205. The laser beam pulse is divided into two by the beam splitter 205 and one of which enters a terahertz electromagnetic wave generating element 100. The terahertz electromagnetic wave generating element 100 which has received the laser beam pulse generates and emits terahertz electromagnetic wave. The terahertz electromagnetic wave reaches a concave reflecting mirror 207, by which it is reflected and converted into a plane wave. The terahertz electromagnetic wave which has been converted into a plane wave is collected by a reflecting mirror 207a and a concave reflecting mirror 207b in such a way that it has a sufficient intensity on an object to be inspected 301. The terahertz electromagnetic wave passes through the object to be inspected 301, is reflected by a concave reflecting mirror 209b, a reflecting mirror 209a and a concave reflecting mirror 209 and collected onto a terahertz detector 211.

Specifications of the femtosecond laser are as below. Center wavelength is 800 nm. Pulse width is 60 to 100 femtoseconds. Pulse rate is 70 to 80 MHz. Output power is 1 watt. A titanium-sapphire laser can be used instead of the femtosecond laser.

The other laser beam pulse divided by the beam splitter 205 passes through an optical delay stage 213, is reflected by a reflecting mirror 215 and reaches the terahertz detector 211. The terahertz detector 211 detects intensity of electric field of terahertz electromagnetic wave received by the terahertz detector 211 when irradiated by the other laser beam pulse. The optical delay stage 213 adjusts time when the other laser beam pulse reaches the terahertz detector 211 by adjusting optical path length through movement of mirrors. Temporal change in intensity of electric field of terahertz electromagnetic wave is measured while time when the other laser beam pulse reaches the terahertz detector 211 is adjusted. Finally, Fourier transform is performed on the temporal change in intensity of electric field, and then change in frequency versus intensity of electric field can be obtained.

Figure 2A:
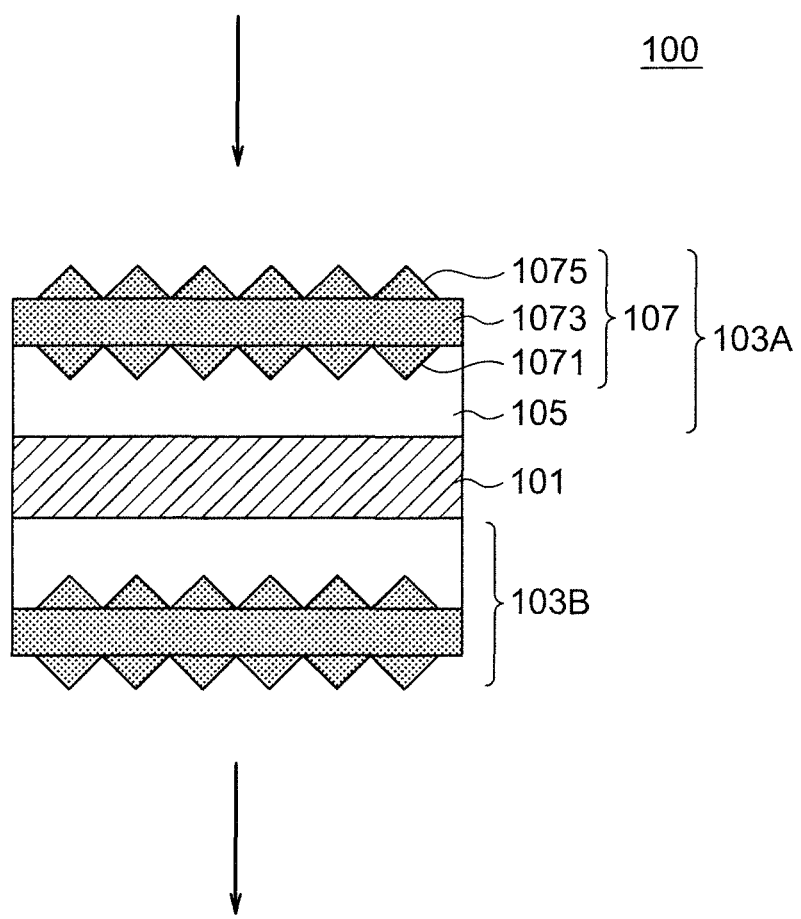
FIG. 2A illustrates a construction of the terahertz electromagnetic wave generating element according to an embodiment of the present invention.

FIG. 2A illustrates a construction of the terahertz electromagnetic wave generating element 100 according to an embodiment of the present invention.

One side of the terahertz electromagnetic wave generating element 100 receives laser beam and the opposite side emits terahertz electromagnetic wave. The side which receives laser beam is called a receiving surface while the side which emits terahertz electromagnetic wave is called an emitting surface hereinafter. The terahertz electromagnetic wave generating element 100 includes nonlinear optical crystal 101, a layer structure 103A provided on the receiving surface side of the nonlinear optical crystal 101 and a layer structure 103B provided on the emitting surface side of the nonlinear optical crystal 101. The layer structure 103A includes a first layer 105, a second layer 1073 provided on the side opposite to the nonlinear optical crystal 101 of the first layer 105, a grating 1071 on a surface on the first layer 105 side, of the second layer 1073 and a grating 1075 on a surface on the side opposite to the first layer 105, of the second layer 1073. The layer structure 103B has a structure similar to the layer structure 103A. The layer structure 103A and layer structure 103B are called a pair of layer structures.

The nonlinear optical crystal 101 is crystal of zinc telluride (ZnTe), for example. Crystal of lithium niobate ($LiNbO_3$), that of gallium phosphide (GaP), that of gallium selenide (GaSe) and the like may be used as inorganic nonlinear optical crystal. Further, crystal of DAST (4-dimethyl amino-N-methyl-4-stilbazolium tosylate) may be used.

Refractive index of a medium of the first layer 105 is less than that of the second layer 1073. In other words, the first layer 105 is made of a material of lower refractive index while the second layer 1073 is made of a material of higher refractive index. When a layer having an appropriate thickness, which is made of a material of lower refractive index and another layer having an appropriate thickness, which is made of a material of higher refractive index are provided, reflected wave of the terahertz electromagnetic wave generated in the nonlinear optical crystal 101, on the interface between the nonlinear optical crystal 101 and the first layer 105 and that on the interface between the second layer 1073 and the surroundings cancel each other out so that decrease in output due to reflection of the terahertz electromagnetic wave can be prevented.

Air is selected as the medium of the first layer 105. In order to prevent decrease in radiation intensity due to reflection on a surface of the nonlinear optical crystal 101, a medium having an appropriate refractive index has to be selected as a medium of the second layer 1073. However, refractive index of a material tends to increase in a frequency range of terahertz electromagnetic wave. For example, aluminum oxide ($Al_2O_3$) and titanium dioxide ($TiO_2$) are typical thin film materials. Refractive index of the former is 1.7 and that of the latter is 2.0 for visible light while refractive index of the former is 3.3 and that of the latter is 10.5 for electromagnetic wave of frequency of 0.45 THz (wavelength of 670 micrometers). Thus, a material having an appropriate refractive index in the terahertz electromagnetic wave range can hardly be found. When a difference between refractive index of the first layer 105 and that of the second layer 1073 is large, reflection on the interface between the first layer 105 and the second layer 1073 is large so that output of terahertz electromagnetic wave is reduced.

Therefore, in the present embodiment, a first grating 1071 is provided on a surface on the side of the nonlinear optical crystal 101, of the second layer 1073 and a second grating 1075 is provided on a surface on the side opposite to the nonlinear optical crystal 101, of the second layer 1073. Grating period of the first grating 1071 and that of the second grating 1075 are set smaller than the wavelength of the used terahertz electromagnetic wave. Such a construction prevents reflection diffracted light and transmission diffracted light from generating so that zero order light alone can be generated.

As shown in FIG. 2A, spaces between protruding portions of the first grating 1071 are filled with air which is the medium of the first layer. The average refractive index of the first grating 1071 or the portion consisting of protruding portions of the second layer 1073 and air is approximately given by the following expressions.

$$n_{TE}(h) = \sqrt{(1 - F(h))n_1(h)^2 + F(h)n_2(h)^2} \quad (1)$$

$$n_{TM}(h) = \sqrt{\dfrac{\dfrac{1}{\dfrac{(1-F(h))}{n_1(h)^2} + \dfrac{F(h)}{n_2(h)^2}}\cos\theta + ((1-F(h))n_1(h)^2 + F(h)n_2(h)^2)\sin\theta}{\cos\theta + \sin\theta}} \quad (2)$$

Average refractive index for TE polarization is represented as $n_{TE}$ while average refractive index for TM polarization is represented as $n_{TM}$. Height along a protrusion portion of the grating above the surface of the second layer 1073 is represented as h. Refractive index of a protrusion portion of the grating at height of h is represented $n_2(h)$ while refractive index of the medium surrounding protrusion portions (air) is represented as $n_1(h)$. Grating period is represented as $\Lambda$. In a cross section which contains vertexes of protrusion portions of the grating and is perpendicular to the surface of the second layer 1073 on which the protrusion portions are provided, a ratio (a duty ratio) of an area occupied by the protrusion portions to the whole area in one period at height of h is represented as the following expression.

$$F(h) = f(h)/\Lambda$$

Angle of incidence of light is represented as $\theta$.

Figure 3:
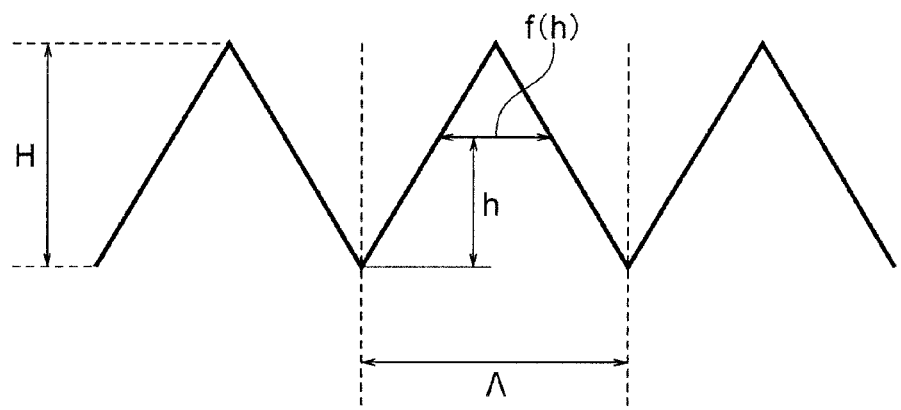
FIG. 3 illustrates duty ratio.

FIG. 3 illustrates duty ratio. When h=0, that is, on the surface of the second layer 1073 on which the protrusion portions of the grating are provided, the duty ratio is 1. At the height of the vertexes of the protrusion portions of the grating, the duty ratio is 0. As h changes from the height of the vertex of the protrusion portion of the grating (H) to 0, the duty ratio continuously changes from 0 to 1. In FIG. 3, a shape of a protrusion portion of the grating in the cross section which contains vertexes of protrusion portions of the grating and is perpendicular to the surface of the second layer 1073 on which the protrusion portions are provided, is triangular. In general, a shape of a protrusion portion of the grating in the cross section may be of any shape by which the duty ratio continuously changes from 0 to 1 as h changes from the height of the vertex of the protrusion portion of the grating (H) to 0.

According to Expression (1), as the duty ratio continuously changes from 0 to 1, average refractive index for TE polarization $n_{TE}$ changes from $n_1(H)$ to $n_2(0)$. According to Expression (2), as the duty ratio continuously changes from 0 to 1, average refractive index for TM polarization $n_{TM}$ changes from $n_1(H)$ to $n_2(0)$.

Thanks to the grating thus provided, average refractive index continuously changes from the refractive index of the medium of the first layer 105 to that of the second layer 1073. Accordingly, reflection on the interface between the first layer 105 and the second layer 1073 can be prevented.

In the description above, a material of the protruding portions of the grating is the same as that of the second layer 1073. Alternatively, a material of the protruding portions of the grating may be different from that of the second layer 1073. In that case, refractive index of a material of the protruding portions of the grating is selected to be close to that of the second layer 1073 such that refractive index gradually changes from that of the first layer 105 to that of the second layer 1073 or in other words, refractive index does not change abruptly.

By way of example, polypropylene is used for the second layer 1073. The reason why polypropylene is used for the second layer 1073 is that it is low in moisture absorbency, a thin film of a large area can easily be made from it and its refractive index in the range of terahertz electromagnetic wave is relatively small compared with other plastics. Refractive index of polypropylene for electromagnetic wave of frequency of 1.5 THz (wavelength of 200 micrometers) is 1.48. Other plastics which can easily be processed and refractive index of which is relatively low in the range of terahertz electromagnetic wave are poly-methyl methacrylate (its refractive index for the above-described frequency is approximately 2.5), polyethylene (its refractive index for the above-described frequency is approximately 2.4), polycarbonate (its refractive index for the above-described frequency is approximately 2.6), polystyrene (its refractive index for the above-described frequency range is approximately 2.6) or the like and they can be used.

Grating is one-dimensionally or two-dimensionally arranged on the surface of the second layer 1073.

Figure 4:
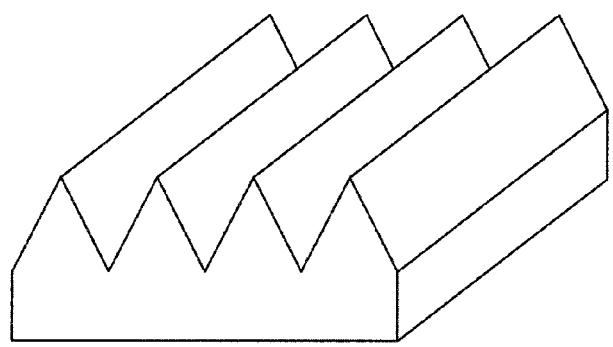
FIG. 4 shows a one-dimensionally arranged grating.

FIG. 4 shows a one-dimensionally arranged grating. The one-dimensionally arranged grating increases output of terahertz electromagnetic wave having a predetermined plane of polarization. More specifically, terahertz electromagnetic wave having a plane of polarization which is perpendicular to the longitudinal direction of the protrusion portions of the grating one-dimensionally arranged can be prevented from decaying.

FIGS. 5A to 5D show two-dimensionally arranged gratings. The two-dimensionally arranged gratings increase output of terahertz electromagnetic wave independently of orientation of the plane of polarization. FIG. 5A shows a two-dimensionally arranged grating in which pyramid protrusion portions are arranged like tetragonal lattice. FIG. 5B shows a two-dimensionally arranged grating in which circular cone protrusion portions are arranged like tetragonal lattice. FIG. 5C shows a two-dimensionally arranged grating in which pyramid protrusion portions are arranged like hexagonal lattice. FIG. 5D shows a two-dimensionally arranged grating in which circular cone protrusion portions are arranged like hexagonal lattice.

In the description above, it is assumed that the terahertz electromagnetic wave generating element 100 is provided with a single pair of layer structures in the interests of simplicity. Actually, the terahertz electromagnetic wave generating element 100 is provided with multiple pairs of layer structures.

Figure 2B:
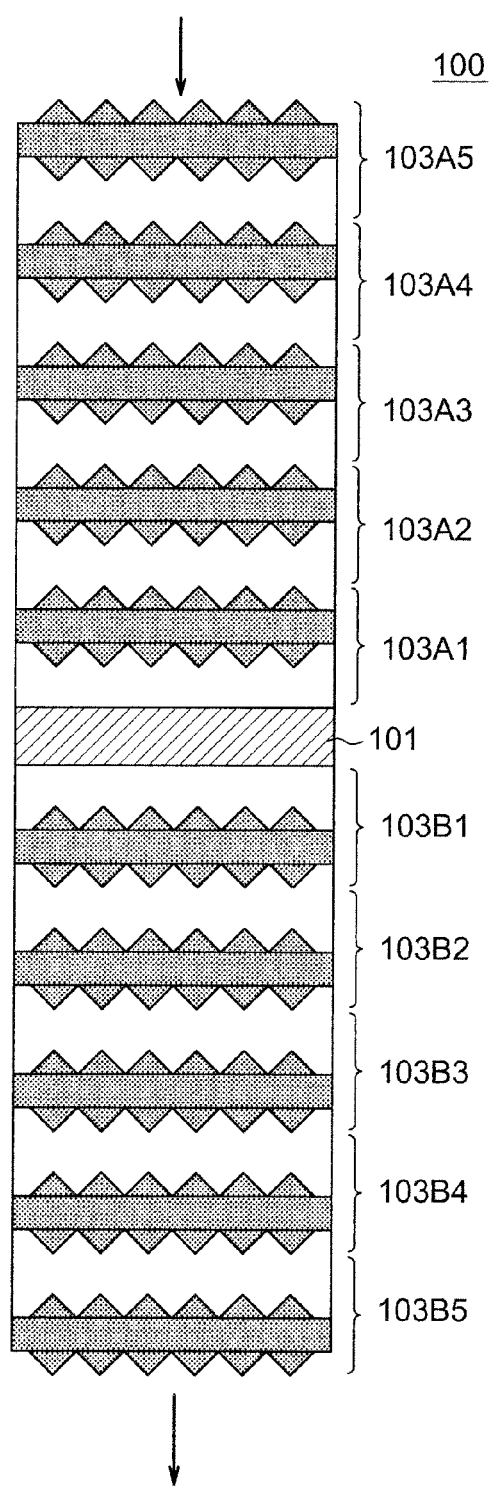
FIG. 2B shows a terahertz electromagnetic wave generating element according to an embodiment of the present invention, which is provided with five pairs of layer structures.

FIG. 2B shows a terahertz electromagnetic wave generating element 100 according to an embodiment of the present invention, which is provided with five pairs of layer structures.

How to design the terahertz electromagnetic wave generating element according to the present invention will be described below. At first, how to design a nonlinear optical crystal which generates terahertz electromagnetic wave having a desired center wavelength will be described. Then, how to design a terahertz electromagnetic wave generating element which generates terahertz electromagnetic wave having a desired band width with the center wavelength set at the center of the band.

FIG. 6 is a flowchart for illustrating how to design a nonlinear optical crystal which generates terahertz electromagnetic wave having a desired center wavelength.

In step S1010 of FIG. 6, a desired center wavelength of terahertz electromagnetic wave to be generated by the terahertz electromagnetic wave generating element is determined.

In step S1020 of FIG. 6, refractive index of the nonlinear optical crystal at the center wavelength of terahertz electromagnetic wave and group index of refraction of the nonlinear optical crystal at the wavelength of the excited pulse laser are obtained.

In step S1030 of FIG. 6, thickness of the nonlinear optical crystal is determined by the following expression using values of the center wavelength, the refractive index and the group index of refraction.

$$L = \frac{\lambda_{THz}}{2|n_g - n_{THz}|} \qquad (3)$$

Thickness of the nonlinear optical crystal is represented as L. The center wavelength of terahertz electromagnetic wave is represented as $\lambda_{THz}$.

Refractive index of the nonlinear optical crystal at the wavelength of $\lambda_{THz}$ is represented as $n_{THz}$. The group index of refraction of the nonlinear optical crystal at the wavelength of the excited pulse laser is represented as $n_g$.

Figure 7:
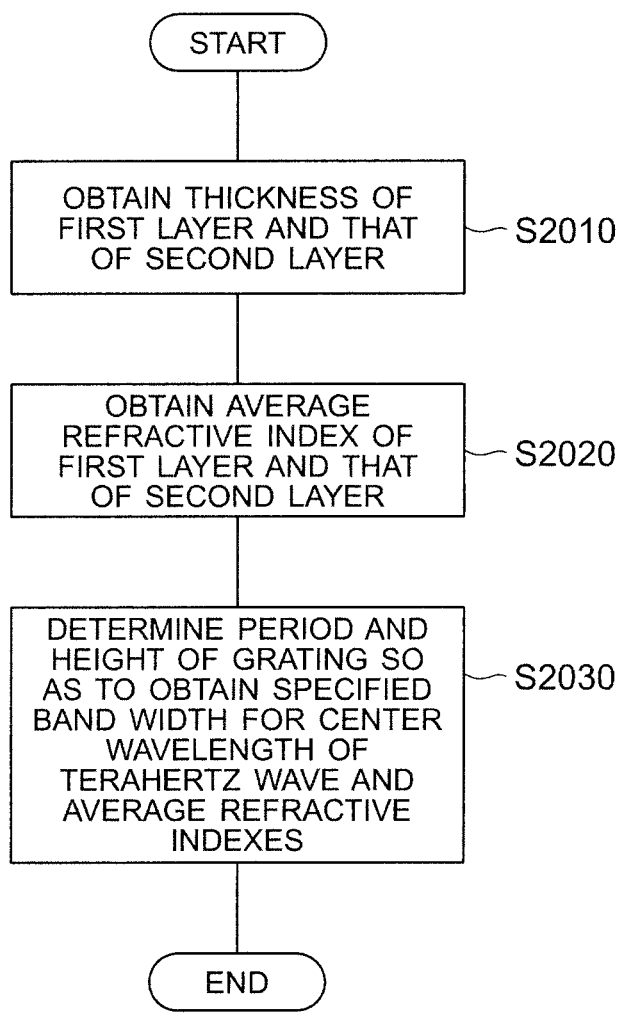
FIG. 7 is a flowchart for illustrating how to design a terahertz electromagnetic wave generating element which generates terahertz electromagnetic wave having a desired band width with the center wavelength
$\lambda_{THz}$.

FIG. 7 is a flowchart for illustrating how to design a terahertz electromagnetic wave generating element which generates terahertz electromagnetic wave having a desired band width with the center wavelength $\lambda_{THz}$ set at the center of the band.

In step S2010 of FIG. 7, thickness $H_1$ of the first layer 105 and thickness $H_2$ of the second layer are determined by the following expressions. Refractive index of the first layer 105 is represented as $n_{105}$ while that of the second layer 1073 is represented as $n_{1073}$.

$$H_1 = \frac{\lambda_{THz}}{4n_{105}} \qquad (4)$$

$$H_2 = \frac{\lambda_{THz}}{4n_{1073}} \qquad (5)$$

That is, thickness $H_1$ of the first layer 105 and thickness $H_2$ of the second layer 1073 are determined in such a way that phase of terahertz electromagnetic wave at the center wavelength is changed by $\pi/2$ or its integral multiple. Phase of terahertz electromagnetic wave at the center wavelength is changed by $2\pi$ when the terahertz electromagnetic wave passes through the first layer 105 and the second layer 1073 on the both sides two times. As a consequence, concerning electromagnetic wave at other values of wavelength than the center wavelength $\lambda_{THz}$, incident wave and its reflected wave cancel each other out, and terahertz electromagnetic wave having the center wavelength $\lambda_{THz}$ alone appears as transmitted light.

In step S2020 of FIG. 7, average refractive index of the first layer and that of the second layer are obtained by the following expression.

$$\bar{n} = \frac{n_{min} + n_{max}}{2} \qquad (6)$$

Refractive index of the first layer and that of the second layer or the protrusion portions of the grating are represented as $n_{min}$ and $n_{max}$.

In step S2030 of FIG. 7, grating height h and grating period $\Lambda$ which generate terahertz electromagnetic wave with the desired band width $W_{THz}$ with the center wavelength $\lambda_{THz}$ of the terahertz electromagnetic wave are determined by the following expression.

$$W_{THz} = \frac{1}{2}\left(1 + \frac{\Lambda}{\lambda_{THz}}\right)\bar{n}h \qquad (7)$$

Expression (7) shows that a band width of frequency is broadened due to change in optical path length when terahertz electromagnetic wave passes through a grating portion having grating height h and an average value of refractive index of $\bar{n}$.

Grating height h and grating period $\Lambda$ have to satisfy the following expressions.

$$\Lambda < \lambda_{THz} - \frac{W_{THz}}{2} \qquad (8)$$

$$h > \frac{W_{THz}}{\left(1 - \frac{W_{THz}}{4\lambda_{THz}}\right)\bar{n}} \qquad (9)$$

Expression (8) means that grating period $\Lambda$ is less than the lower limit of wavelength of the band width. When the grating period $\Lambda$ is equal to or greater than the lower limit of wavelength of the band width, diffracted light is generated, causing decrease in transmittance.

Expression (9) is obtained by eliminating grating period $\Lambda$ of expression (8) using Expression (7). When Expression (9) is not satisfied, high-order diffracted light is generated, causing decrease in transmittance just as in the case that Expression (8) is not satisfied.

The inventor has obtained new findings that the terahertz electromagnetic wave generating element provided with multiple pairs of layer structures shown in FIG. 2B generates terahertz electromagnetic wave with the band width given by Expression (7) and the generated terahertz electromagnetic wave shows a frequency versus utilization factor graph (frequency spectrum) shaped like a rectangular with steep sides corresponding to the both limits of the band as described below, for example. The reason why the shape like a rectangular with steep sides corresponding to the both limits of the band is obtained is as below.

Assume that the second layer 1073 is not provided with a grating in FIG. 2A. In the case of electromagnetic waves at higher frequencies such as those in the range of infrared light or those in the range of visible light, a narrow band width transmittance spectrum with the peak at the center wavelength (frequency) can be obtained when thickness of the first layer and that of the second layer are determined in such a way that Expressions (4) and (5) are satisfied. However, since wavelength of terahertz electromagnetic wave is very large, thickness of layers has to be increased for phase control. As a consequence, travel distance of terahertz electromagnetic wave in the medium is also increased. Increase in travel distance in the medium causes transmission loss and reflection loss like in the case of visible light and infrared light conventionally used and consequent increase in absorption of the terahertz electromagnetic wave travelling in the medium and the like produce a phase shift. Under the influence of the phase shift, the peak frequency also tends to shift. As a consequence, an interfering frequency band gradually shifts as the terahertz electromagnetic wave travels between the layer structures on the both sides of the generating layer, and therefore the rough shape of frequency spectrum obtained is not a rectangular distribution but a Gaussian distribution in which utilization factor gradually changes against frequency.

In the present invention, the gratings 1071 and 1075 are provided on the both sides of the second layer 1073. When the gratings 1071 and 1075 are provided on the both sides of the second layer 1073, a phase shift corresponding to the optical path length in Expression (7)

$\bar{n}h$ is generated for each grating. By the phase shift, the peak frequency shifts by an amount corresponding to the optical path length. In the arrangement in which the gratings are provided on the both sides of the second layer 1073 and the layer structures are provided on the both sides of the generating element 101, correction with a coefficient $$\frac{1}{2}\left(1+\frac{\Lambda}{\lambda_{THz}}\right)$$

is given to an amount of phase shift and the total band width $W_{TH}$ is determined (Expression (7)).

In this system, an amount of shift of the peak frequency is modulated when the light passes through each layer and spectrum in a narrow-band corresponding to the amount of shift is generated. However, since the light passes through each layer at random, spectrum in which narrow-band spectra each of which corresponds to an arbitrary amount of shift overlap one another at random is radiated. In this case, an amount of shift of the peak frequency which is given at random is restricted by phase modulation depending on the structure of the gratings in such a way that the amount of shift does not exceed the band width $W_{TH}$.

Through the phenomena described above, frequency spectrum having a rectangular distribution in which narrow-band spectra overlap one another can be obtained finally.

Effects of the present invention will be examined by simulation. For the simulation, rigorous coupled wave analysis (RCWA) method was used. In the simulation, polarization of electromagnetic wave was assumed to be TE polarization and a one-dimensionally arranged grating was used. Similar results are obtained in the case of TM polarization or a two-dimensionally arranged grating.

EXAMPLE 1

Example 1 is a terahertz electromagnetic wave generating element provided with five pairs of layer structures. The center wavelength of terahertz electromagnetic wave is determined to be 136 micrometers and the center frequency is determined to be 2.2 THz (step S1010 of FIG. 6).

Refractive index $n_{THz}$ of the nonlinear optical crystal at the center frequency and group index of refraction $n_g$ at the wavelength of the excited pulse laser are as below (step S1020 of FIG. 6).

$n_{THz}$=2.92
$n_g$=5.876

Accordingly, thickness of the nonlinear optical crystal is obtained using Expression (3) as below (step S1030 of FIG. 6).

$$L=\frac{136}{2|5.879-2.92|}=23$$

Refractive index of the first layer 105 is 1 ($n_{105}$=1) and refractive index of the second layer 1073 is 1.48 ($n_{1073}$=1.48). From Expressions (4) and (5), thickness $H_1$ of the first layer 105 and thickness $H_2$ of the second layer 1073 are 34 micrometers and 23 micrometers respectively.

Band width (wavelength range) is provisionally assumed to be 38 micrometers. In this case, designed bands are as below.

| | |
|---|---|
| Wavelength band | 117 micrometers-155 micrometers |
| Frequency band | 1.94 THz-2.56 THz |

Grating period is set to 90 micrometers in such a way that Expression (6) is satisfied.

When refractive index of the first layer (refractive index of air, that is 1.0) and that of the second layer (refractive index of polypropylene, that is 1.48) are substituted into Expression (4), the following expression can be obtained (step S2010 of FIG. 7).

$$\bar{n}=\frac{n_{min}+n_{max}}{2}=\frac{1.0+1.48}{2}=1.24$$

Further, grating period, center wavelength and average refractive index are substituted into Expression (5), band wavelength range is 38 micrometers when grating height is 37 micrometers (step S2020 of FIG. 7).

$$W_{THz}\approx\frac{1}{2}\left(1+\frac{\Lambda}{\lambda_{THz}}\right)\bar{n}h=\frac{1}{2}\times\left(1+\frac{90}{136}\right)\times 1.24\times 37=38.1$$

Table 1 shows specifications of the terahertz electromagnetic wave generating element of the present example.

TABLE 1

| (Five pairs of layer structures) | Size | Material |
|---|---|---|
| Nonlinear optical crystal 101 | Thickness 23 micrometers | Zinc telluride |
| First layer 105 | Thickness 34 micrometers | Air |
| Second layer 1073 | Thickness 23 micrometers | Polypropylene |
| First grating 1071 | Period 90 micrometers Height 37 micrometers | Polypropylene |
| Second grating 1075 | Period 90 micrometers Height 37 micrometers | Polypropylene |

Figure 8:
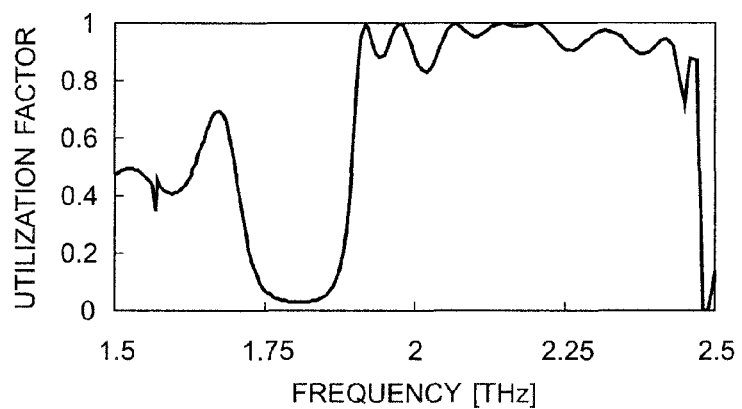
FIG. 8 shows a frequency versus utilization factor relationship of the terahertz electromagnetic wave generating element of Example 1, which is obtained through RCWA.

FIG. 8 shows a frequency versus utilization factor relationship of the terahertz electromagnetic wave generating element of the present example, which is obtained through RCWA. Utilization factor means a ratio of intensity of terahertz electromagnetic wave radiated by the nonlinear optical crystal to theoretical maximum intensity of terahertz electromagnetic wave radiated by the nonlinear optical crystal. That is, utilization factor is that of terahertz electromagnetic wave. The theoretical maximum intensity is represented by second order nonlinear polarization $P^{(2)}(\omega 3)$ of terahertz electromagnetic wave at frequency $\omega 3$ as below when laser beams from the femtosecond laser at frequencies at $\omega 1$ and $\omega 2$ enter the nonlinear optical crystal.

$$P^{(2)}(\omega_3=|\omega_1-\omega_2|)=\epsilon_0\chi^{(2)}(\omega_3)E(\omega_1)E^*(\omega_2)$$

$\epsilon_0$ represents dielectric constant in vacuum, $\chi(2)$ represents second order nonlinear susceptibility of the non-linear optical crystal and

E and

E* represent electric fields.

In FIG. 8, utilization factor is substantially 1 in the frequency band from 1.94 THz to 2.45 THz (the wavelength band from 122 micrometers to 155 micrometers). Thus, the utilization factor distribution close to the designed band width can be obtained.

After values of thickness of the first layer and that of the second layer, grating period (first period) and grating height (first height) have been determined, the above mentioned values can be adjusted while simulation using RCWA is performed to obtain a desired band width.

According to the present embodiment, energy of terahertz electromagnetic wave can be concentrated into a desired band width. Accordingly, detection accuracy of the object inspection system using the terahertz electromagnetic wave generating section shown in FIG. 1 can be increased. More specifically, cocaine which is a prohibited drug has a transmittance of approximately 50% around 2.3 THz while ecgonine which is another prohibited drug has a transmittance of approximately 30% around 2.1 THz. TNT which is an explosive substance has a transmittance of approximately 70% around 2.2 THz. Accordingly, by concentrating energy of terahertz electromagnetic wave into the band width of the present example, the above-described substances can be detected with a high accuracy by the object inspection system.

In FIG. 8, some amount of terahertz electromagnetic wave is generated in the frequency range at or below 1.75 THz besides terahertz electromagnetic wave generated in the desired band width. Such terahertz electromagnetic wave below the desired band width can be removed from the optical system by deflecting beam as diffracted light using a diffraction grating.

The band to be removed is the frequency band at or below 1.75 THz or the wavelength band at or above 171.5 micrometers. On the other hand, the desired band is at or above 1.94 THz or at or below 155 micrometers in wavelength. Accordingly, period of the diffraction grating $\Lambda_d$ is determined as below.

$$155 < \Lambda_d < 171.5$$

Terahertz electromagnetic wave in the desired band width passes through the diffraction grating with the above-described period as 0-order light. Terahertz electromagnetic wave in the band to be removed is deflected as diffracted light and therefore can be removed from the optical system. Thus, in order to remove terahertz electromagnetic wave at frequencies above the upper limit of the desired band width, the grating period should be made closer to the lower limit of the expression described above.

EXAMPLE 2

Example 2 is a terahertz electromagnetic wave generating element provided with nine pairs of layer structures. Just as in the case of Example 1, the center wavelength of terahertz electromagnetic wave is determined to be 136 micrometers and the center frequency is determined to be 2.2 THz. Thickness of the first layer 105 and that of the second layer 1073 are determined to be 34 micrometers and 23 micrometers, respectively.

Table 2 shows specifications of the terahertz electromagnetic wave generating element of the present example. The specifications are identical with those of Example 1 except the number of pairs.

TABLE 2

| (Nine pairs of layer structures) | Size | Material |
| --- | --- | --- |
| Nonlinear optical crystal 101 | Thickness 23 micrometers | Zinc telluride |
| First layer 105 | Thickness 34 micrometers | Air |
| Second layer 1073 | Thickness 23 micrometers | Polypropylene |
| First grating 1071 | Period 90 micrometers Height 37 micrometers | Polypropylene |
| Second grating 1075 | Period 90 micrometers Height 37 micrometers | Polypropylene |

Figure 9:
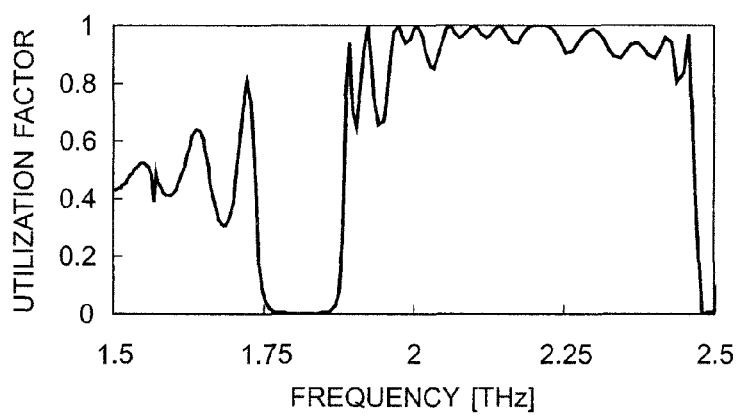
FIG. 9 shows a frequency versus utilization factor relationship of the terahertz electromagnetic wave generating element of Example 2 which is obtained through RCWA.

FIG. 9 shows a frequency versus utilization factor relationship of the terahertz electromagnetic wave generating element of the present example, which is obtained through RCWA.

In FIG. 9, utilization factor is substantially 1 in the frequency band from 1.94 THz to 2.45 THz (the wavelength band from 122 micrometers to 155 micrometers). Thus, the obtained utilization factor distribution is close to the designed band width (1.94 THz to 2.56 THz). As discussed earlier, by the use of a terahertz electromagnetic wave generating element provided with multiple layer structures, electromagnetic wave within a desired band width can be generated. In general, the larger the number of pairs is, the steeper the both sides of a rectangle like shape of the graph showing a frequency versus utilization factor relationship is.

EXAMPLE 3

Example 3 is a terahertz electromagnetic wave generating element provided with three pairs of layer structures. Just as in the case of Example 1, the center wavelength of terahertz electromagnetic wave is determined to be 136 micrometers and the center frequency is determined to be 2.2 THz. Thickness of the first layer 105 and that of the second layer 1073 are determined to be 34 micrometers and 23 micrometers, respectively.

Table 3 shows specifications of the terahertz electromagnetic wave generating element of the present example. The specifications are identical with those of Example 1 except the number of pairs.

TABLE 3

| (Three pairs of layer structures) | Size | Material |
| --- | --- | --- |
| Nonlinear optical crystal 101 | Thickness 23 micrometers | Zinc telluride |
| First layer 105 | Thickness 34 micrometers | Air |
| Second layer 1073 | Thickness 23 micrometers | Polypropylene |
| First grating 1071 | Period 90 micrometers Height 37 micrometers | Polypropylene |

TABLE 3-continued

| (Three pairs of layer structures) | Size | Material |
|---|---|---|
| Second grating 1075 | Period 90 micrometers Height 37 micrometers | Polypropylene |

Figure 10:
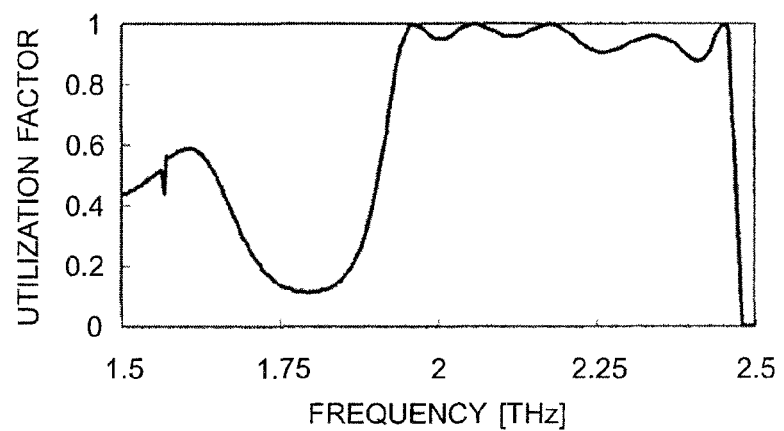
FIG. 10 shows a frequency versus utilization factor relationship of the terahertz electromagnetic wave generating element of Example 3, which is obtained through RCWA.

FIG. 10 shows a frequency versus utilization factor relationship of the terahertz electromagnetic wave generating element of the present example, which is obtained through RCWA.

In FIG. 10, utilization factor is substantially 1 in the frequency band from 1.94 THz to 2.45 THz (the wavelength band from 122 micrometers to 154 micrometers). Thus, the obtained utilization factor distribution is close to the designed band width (1.94 THz to 2.56 THz). As discussed earlier, by the use of a terahertz electromagnetic wave generating element provided with multiple layer structures, electromagnetic wave within a desired band width can be generated.

EXAMPLE 4

Example 4 is a terahertz electromagnetic wave generating element provided with five pairs of layer structures. Just as in the case of Example 1, the center wavelength of terahertz electromagnetic wave is determined to be 136 micrometers and the center frequency is determined to be 2.2 THz. Thickness of the first layer 105 and that of the second layer 1073 are determined to be 34 micrometers and 23 micrometers, respectively.

Band width (wavelength range) is provisionally assumed to be 6 micrometers. In this case, designed bands are as below.
Wavelength band 133 micrometers-139 micrometers
Frequency band 2.16 THz-2.25 THz
Grating period is set to 90 micrometers in such a way that Expression (6) is satisfied.

When refractive index of the first layer (refractive index of air, that is 1.0) and that of the second layer (refractive index of polypropylene, that is 1.48) are substituted into Expression (4), the following expression can be obtained (step S2010 of FIG. 7).

$$\bar{n} = \frac{n_{min} + n_{max}}{2} = \frac{1.0 + 1.48}{2} = 1.24$$

Further, grating period, center wavelength and average refractive index are substituted into Expression (5), band wavelength range is 6.18 micrometers when grating height is 6 micrometers (step S2020 of FIG. 7).

$$W_{THz} \approx \frac{1}{2}\left(1 + \frac{\Lambda}{\lambda_{THz}}\right)\bar{n}h = \frac{1}{2} \times \left(1 + \frac{90}{136}\right) \times 1.24 \times 6 = 6.18$$

Table 4 shows specifications of the terahertz electromagnetic wave generating element of the present example.

TABLE 4

| (Five pairs of layer structures) | Size | Material |
|---|---|---|
| Nonlinear optical crystal 101 | Thickness 23 micrometers | Zinc telluride |
| First layer 105 | Thickness 34 micrometers | Air |
| Second layer 1073 | Thickness 23 micrometers | Polypropylene |
| First grating 1071 | Period 90 micrometers Height 6 micrometers | Polypropylene |
| Second grating 1075 | Period 90 micrometers Height 6 micrometers | Polypropylene |

Figure 11:
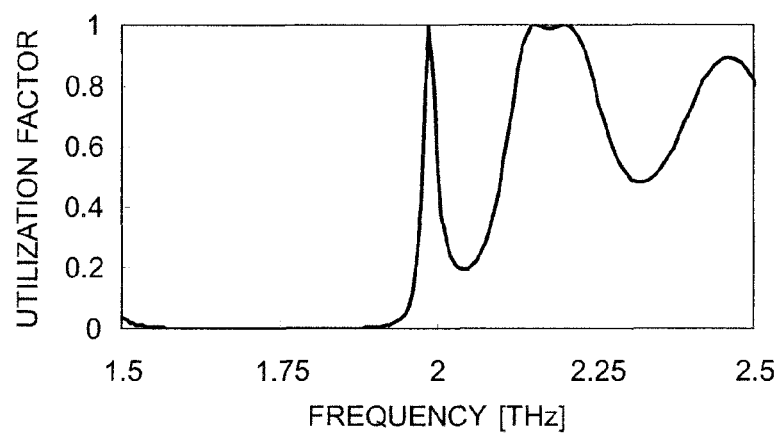
FIG. 11 shows a frequency versus utilization factor relationship of the terahertz electromagnetic wave generating element of Example 4, which is obtained through RCWA.

FIG. 11 shows a frequency versus utilization factor relationship of the terahertz electromagnetic wave generating element of the present example, which is obtained through RCWA.

In FIG. 11, utilization factor is substantially 1 in the frequency band from 2.13 THz to 2.25 THz (the wavelength band from 133 micrometers to 141 micrometers). Thus, the obtained utilization factor distribution is close to the designed band width (2.16 THz to 2.25 THz).

When comparing the present example with Example 1, it can be understood that the band width can be changed as desired by changing the grating height.

Manufacturing Methods of Terahertz Electromagnetic Wave Generating Element

At first, a manufacturing method of a grating will be described. When manufacturing a grating, a mold for the grating is manufactured by machining or lithography process. When the mold of the grating is manufactured by machining process, a mold substrate made of metal or glass is machined using diamond tool into a specified profile with projections and depressions. Since period of diffraction grating used for terahertz electromagnetic wave is from 30 micrometers to 3 millimeters, machining process can be used. When the mold of the grating is manufactured by lithography process, a resist is coated on a mold substrate and the substrate is illuminated with electron rays or lights while the exposure is modulated depending on a specified profile with projections and depressions. When the illuminated resist is developed, some portions of the resist are removed according to exposure modulation and a profile with projections and depressions of the resist is formed. Finally, the profile with projections and depressions of the resist is transferred to the mold substrate and the specified profile with projections and depressions is formed on the mold substrate.

Figure 12A:
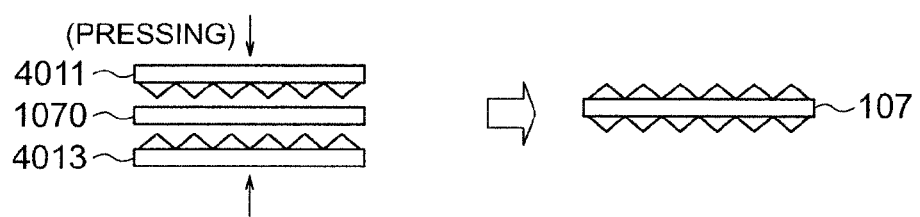
FIG. 12A illustrates how to manufacture the second layer provided with gratings by imprinting process.
Figure 12B:
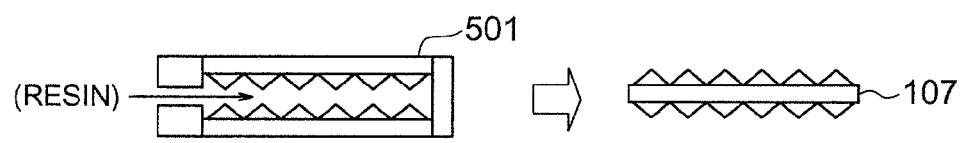
FIG. 12B illustrates how to manufacture the second layer provided with gratings by injection molding.

FIGS. 12A and 12B illustrate how to manufacture a grating which is incorporated into a terahertz electromagnetic wave generating element by the use of the mold manufactured in the way described above.

FIG. 12A illustrates how to manufacture the second layer provided with gratings by imprinting process. When the second layer provided with gratings is manufactured by imprinting process, molds 4011 and 4013 are pressed onto a substrate 1070 made of a high refractive index medium such as polypropylene, and the molds are heated (thermal imprinting) or the substrate is illuminated (photo cure imprinting). As a consequence, the profiles of gratings are transferred onto the substrate 1070 and then the second layer 107 provided with gratings is manufactured. By imprinting, a diffraction grating structure in a large area can be manufactured when the substrate 1070 is shaped like a film. Further, manufacturing in volume is possible by the use of a method called roll imprinting in which the molds 4011 and 4013 are arranged like rolls and the substrate 1070 shaped like a film is forced to pass through a space between the molds which are rotating.

FIG. 12B illustrates how to manufacture the second layer provided with gratings by injection molding. When diffraction gratings are manufactured by injection molding, resin is injected into a mold 501 and then the mold is released to obtain the second layer 107 provided with gratings.

Figure 13:
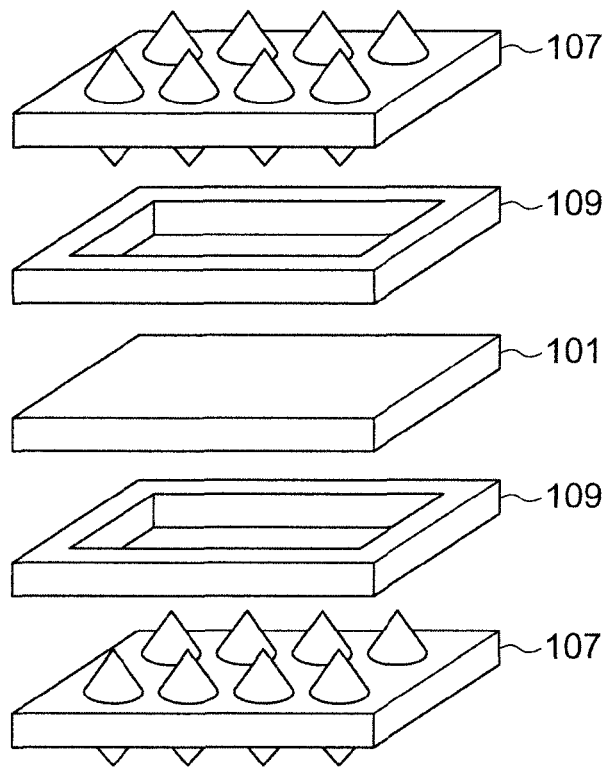
FIG. 13 illustrates how to manufacture a terahertz electromagnetic wave generating element using the second layer manufactured in the way described above.

FIG. 13 illustrates how to manufacture a terahertz electromagnetic wave generating element using the second layer 107 manufactured in the way described above.

A frame 109 for forming the first layer 105 the medium of which is air is stuck on a face of the nonlinear optical crystal plate 101. Further, the second layer 107 is stuck on the surface of the frame 109 which is opposite to the surface on which the nonlinear optical crystal plate 101 is stuck. Such a terahertz electromagnetic wave generating element having multiple layer structures as shown in FIG. 2B can be manufactured by piling up and bonding together layer structures each of which is made of the frame 109 and the second layer 107.

Figure 14:
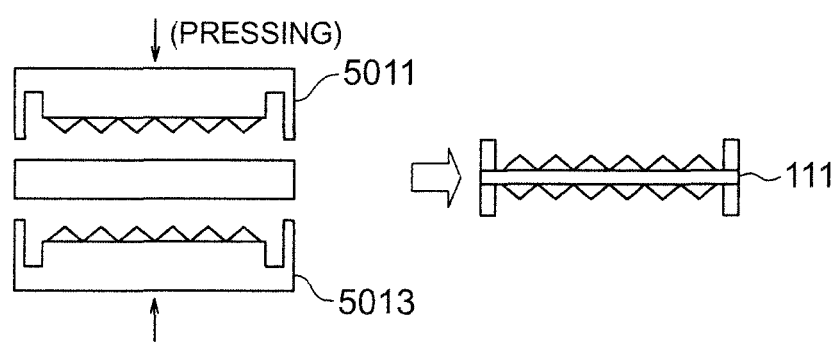
FIG. 14 illustrates how to integrally manufacture the second layer provided with gratings and the frame for forming the first layer.

FIG. 14 illustrates how to integrally manufacture the second layer provided with gratings and the frame for forming the first layer by imprinting process. Molds 5011 and 5013 which have profiles of the gratings and the frame are pressed onto the substrate 1070 made of a high refractive index medium such as polypropylene, and the molds are heated (thermal imprinting) or the substrate is illuminated (photo cure imprinting). As a consequence, the profiles of gratings are transferred onto the substrate 1070 and the second layer 107 provided with gratings and the frame for forming the first layer are integrally manufactured.

Figure 15:
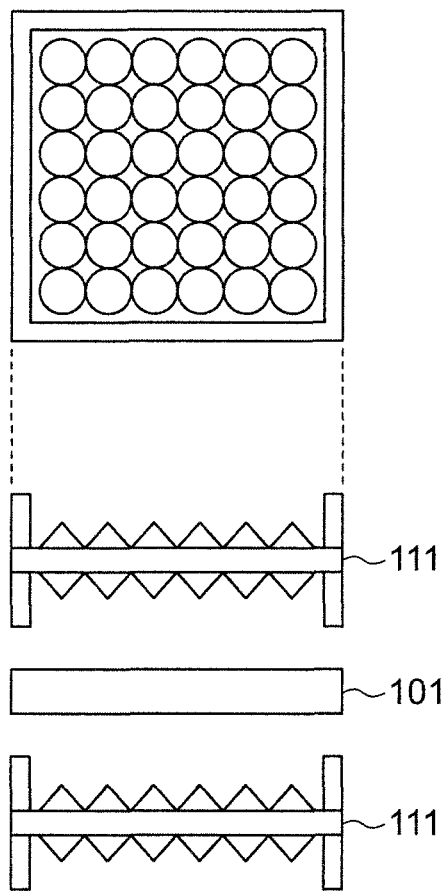
FIG. 15 illustrates how to manufacture a terahertz electromagnetic wave generating element using the second layer and the frame which are integrally formed.

FIG. 15 illustrates how to manufacture a terahertz electromagnetic wave generating element using the second layer 107 and the frame 111 which are integrally formed.

A portion in which the second layer 107 and the frame 111 are integrally formed is stuck on a surface of the nonlinear optical crystal plate 101. Such a terahertz electromagnetic wave generating element having multiple layer structures as shown in FIG. 2B can be manufactured by piling up and bonding together portions corresponding to layer structures, in each of which the second layer 107 and the frame 111 are integrally formed.

What is claimed is:

1. A terahertz electromagnetic wave generating element comprising:
    a generating layer made of nonlinear optical substance which emits terahertz electromagnetic wave from a surface when another surface is illuminated by light; and
    a multiple pairs of layer structures provided on the both sides of the generating layer, wherein each of the multiple pairs of layer structures comprises;
    a first layer;
    a second layer provided on a side of the first layer, the side being opposite to the side of the generating layer;
    a first grating provided on a surface on the generating layer side of the second layer, the first grating having a first period smaller than wavelength of used terahertz electromagnetic wave and a first height; and
    a second grating provided on a surface on the side opposite to the generating layer of the second layer, the second grating having the first period and the first height;
    wherein refractive index of a medium of the first layer (a first refractive index) is smaller than refractive index of a medium of the second layer (a second refractive index), the first grating and the second grating are constructed in such a way that refractive index between the first layer and the second layer gradually changes between the first refractive index and the second refractive index and thickness of the first layer, thickness of the second layer and the first height are determined in such a way that terahertz electromagnetic wave having a desired band width is generated around the center wavelength of the generated terahertz electromagnetic wave.

2. A terahertz electromagnetic wave generating element according to claim 1 wherein the first period is determined in such a way that terahertz electromagnetic wave of frequencies on and above the upper limit of the desired band width is removed as much as possible.

3. A terahertz electromagnetic wave generating element according to claim 1 wherein protruding portions of the first and second gratings are made of the same material as a material of the second layer.

4. A terahertz electromagnetic wave generating element according to claim 1 wherein the first and second gratings are one-dimensionally arranged.

5. A terahertz electromagnetic wave generating element according to claim 1 wherein the first and second gratings are two-dimensionally arranged.

6. A terahertz electromagnetic wave generating element according to claim 1 wherein a medium of the first layer is air.

7. A terahertz electromagnetic wave generating element according to claim 6 wherein a support shaped like a frame is provided to form the first layer.

8. A terahertz electromagnetic wave generating element according to claim 7 wherein the second layer and the support shaped like a frame are integrally formed.

9. A terahertz electromagnetic wave generating element according to claim 1 wherein a medium of the second layer is polypropylene.

10. A terahertz electromagnetic wave generating element according to claim 1 wherein the nonlinear optical substance is crystal of zinc telluride (ZnTe).

11. An object inspection system comprising the terahertz electromagnetic wave generating element recited in claim 1.

* * * * *